United States Patent
Ebner et al.

(10) Patent No.: US 7,022,070 B2
(45) Date of Patent: Apr. 4, 2006

(54) METHOD FOR CONTINUOUS MONITORING OF PATIENTS TO DETECT THE POTENTIAL ONSET OF SEPSIS

(75) Inventors: Dennis M. Ebner, Sisters, OR (US); Jack E. McKenzie, Bend, OR (US)

(73) Assignee: Mini-Mitter Co., Inc., Bend, OR (US)

( * ) Notice: Subject to any disclaimer, the term of this patent is extended or adjusted under 35 U.S.C. 154(b) by 67 days.

(21) Appl. No.: 10/393,455

(22) Filed: Mar. 19, 2003

(65) Prior Publication Data

US 2003/0181815 A1   Sep. 25, 2003

Related U.S. Application Data

(60) Provisional application No. 60/367,076, filed on Mar. 22, 2002, provisional application No. 60/394,340, filed on Jul. 3, 2002.

(51) Int. Cl.
*A61B 5/00* (2006.01)
(52) U.S. Cl. ............ 600/301; 600/500; 600/508; 600/529; 600/549
(58) Field of Classification Search ............ 600/300, 600/301, 500–503, 529, 549
See application file for complete search history.

(56) References Cited

U.S. PATENT DOCUMENTS

| | | | | |
|---|---|---|---|---|
| 3,618,592 A | * | 11/1971 | Stewart | 600/484 |
| 4,763,663 A | * | 8/1988 | Uphold et al. | 600/484 |
| 4,844,076 A | * | 7/1989 | Lesho et al. | 600/302 |
| 5,385,529 A | * | 1/1995 | Koch | 600/22 |
| 6,102,856 A | * | 8/2000 | Groff et al. | 600/301 |
| 6,416,471 B1 | * | 7/2002 | Kumar et al. | 600/300 |
| 2002/0107436 A1 | * | 8/2002 | Barton et al. | 600/382 |

OTHER PUBLICATIONS

Spandorfer et al. "Sugar and Spice and Everything Nice", Pediatric Annals. Oct. 2001; 30, 10: Health & Medical Complete, pp. 603-606.*

(Continued)

*Primary Examiner*—Robert L. Nasser
*Assistant Examiner*—Patricia Mallari
(74) *Attorney, Agent, or Firm*—John Smith-HIll; Smith-Hill and Bedell

(57) ABSTRACT

A method of screening for possible onset of sepsis in a patient includes providing the patient with a transducer that automatically and periodically measures a first physiological parameter of the patient and transmits a first signal that is encoded with the measured parameter value, and receiving the first signal and automatically comparing the measured parameter value with at least one alarm limit. The first physiological parameter is body temperature, heart rate, respiration rate or a clinical indicator of sepsis. A conditional warning signal is asserted in the event that the measured parameter value bears a predetermined relationship to said alarm limit and an alarm signal is issued in the event that a physiological condition other than the condition that gave rise to the conditional warning signal is indicative of onset of sepsis.

6 Claims, 3 Drawing Sheets

OTHER PUBLICATIONS

Beal et al. "Multiple organ failure syndrome in the 1990s", JAMA. Chicago: Jan. 19, 1994, v. 271, iss. 3, pp. 226-234.*

Creechan et al. "Cooling by Convection Vs. Cooling by Conduction for Treatment of Fever in Critically Ill Adults", American Journal of Critical Care; Jan. 2001; vol. 10, No. 1, pp. 52-59.*

Bone et al. "Definitions for Sepsis and organ failure and guidelines for the use of innovative therapies in sepsis", Chest. Jun. 1992.*

"Urosepsis, Septicemia, Urinary Tract Infection (UTI) Audit Tool" NMMRA, Feb. 27, 2002, p. 2.*

Finkelstein et al. "Fever in Pediatric Primary Care: Occurrence, Management, and Outcomes", Pediatrics. Jan. 2000; vol. 105, No. 1, pp. 260-266.*

Sands et al. "Epidemiology of Sepsis Syndrome in 8 Academic Medical Centers" JAMA. Jul. 16, 1997; vol. 278, No. 3; pp. 234-240.*

Rangel-Frausto et al. "The Natural History of Systemic Inflammatory REsponse Syndrome (SIRS)" JAMA. Jan. 11, 1995; Col. 273, No. 2; pp. 117-123.*

Bauer et al. "Effect of Sepsis Syndrome on Neonatal Oxygen Consumption and Energy Expenditure," Pediatrics Dec. 2002. vol. 11, No. 6. pp. 1-4.*

* cited by examiner

METHOD FOR CONTINUOUS MONITORING OF PATIENTS TO DETECT THE POTENTIAL ONSET OF SEPSIS

CROSS-REFERENCE TO RELATED APPLICATIONS

This application claims benefit of U.S. Provisional Application No. 60/367,076 filed Mar. 22, 2002 and U.S. Provisional Application No. 60/394,340 filed Jul. 3, 2002, the entire disclosure of each of which is hereby incorporated by reference herein for all purposes.

BACKGROUND OF THE INVENTION

This invention relates to a method for continuous monitoring of patients to detect the potential onset of sepsis.

Sepsis is a medical condition in which bacteria invade the body causing a serious infection. Large and increasing numbers of microorganisms overwhelm the body's defense systems and actively multiply in the bloodstream. Sepsis is associated with a large stress on the body, such as trauma.

Over 684,000 cases of sepsis were reported in the United States in 1998. The mortality rate for these cases was 17.4%. Overall, sepsis is the 11th leading cause of death in the U.S. and the annual cost of providing care for this condition is approximately $15 billion.

Sepsis is almost always accompanied by an increase or decrease in body core temperature as well as elevation in pulse and respiration rates.

Current hospital care protocols for detecting onset of sepsis require periodic body temperature, pulse rate, and respiration rate monitoring, and patient observation. A typical sepsis screening criterion used by healthcare providers is as follows:

a. Body core temperature greater than 38.3° C. (about 101° F.) or less than 35.6° C. (about 96° F.).
b. Heart rate greater than 90 beats per minute.
c. Respiration rate greater than 20 respirations per minute.
d. Clinical evidence of infection, such as redness around an infection site, swelling, or facial pallor.

The presence of any two of these four factors is considered to be an indication of the potential onset of sepsis, rendering further patient evaluation, including blood cultures and chest x-rays, desirable. If the further evaluation confirms the diagnosis of sepsis, the accepted clinical treatment is the administration of substantial doses of intravenous antibiotics.

Early detection of sepsis and appropriate administration of antibiotics can greatly reduce the mortality rate of this disease.

For a patient who has not been admitted to a critical care unit or intensive care unit, the intervals at which body temperature, heart rate and respiration rate are measured during hospitalization can be quite long and quite variable and may depend on circumstances other than the current condition of the patient, such as the workload of nurses and other healthcare professionals.

It can be appreciated that more frequent body temperature, heart rate and respiration rate monitoring could be helpful in detecting the possible onset of sepsis so that a rapid diagnosis and immediate care can be provided to thwart this disease from rapidly overwhelming the patient's immune system.

U.S. patent application Ser. No. 10/017,098 discloses a digital sensor for a miniature medical thermometer and body temperature monitor. This digital sensor can be implemented in a pill that can be ingested for measuring body core temperature, in a small skin patch for measuring skin temperature, or in a capsule that can be placed in a body orifice, such as the ear canal.

U.S. patent application Ser. No. 10/071,534 discloses a skin patch including a telesensor for emitting a signal that represents a physiological parameter sensed by the telesensor. The physiological parameters that can be sensed by an appropriate telesensor include body temperature and ECG voltage. It is known that heart rate and respiration rate can be derived from the ECG voltage waveform.

SUMMARY OF THE INVENTION

In accordance with a first aspect of the invention there is provided a method of screening for possible onset of sepsis in a patient, comprising (a) providing the patient with a transducer that automatically and periodically measures a first physiological parameter of the patient and transmits a first signal that is encoded with the measured parameter value, (b) receiving the first signal and automatically comparing the measured parameter value with at least one alarm limit, (c) asserting a conditional warning signal in the event that the measured parameter value bears a predetermined relationship to said alarm limit, and (d) issuing an alarm signal in the event that another physiological condition is indicative of onset of sepsis, and wherein said first physiological parameter is body temperature, heart rate, respiration rate or a clinical indicator of sepsis.

In accordance with a second aspect of the invention there is provided a method of screening for possible onset of sepsis in a patient, comprising (a) providing the patient with a first transducer that automatically and periodically measures the patient's core temperature and transmits a first signal that is encoded with the measured core temperature value, (b) providing the patient with a second transducer that automatically and periodically measures a reference temperature of the patient and transmits a second signal that is encoded with the measured reference temperature value, (c) receiving the first and second signals and automatically comparing the measured core temperature value with the measured reference temperature value, (d) issuing a warning signal in the event that the measured temperature value bears a predetermined relationship to the measured reference temperature value, and (e) testing the patient for onset of sepsis.

In accordance with a third aspect of the invention there is provided a method of screening for possible onset of sepsis in a patient, comprising (a) providing the patient with a transducer that automatically measures the patient's interbeat interval, (b) calculating the patient's heart rate variability, (c) issuing a warning signal in the event that the calculated value of heart rate variability bears a predetermined relationship to a reference value, and (d) testing the patient for onset of sepsis.

In accordance with a fourth aspect of the invention there is provided a method of screening and testing for sepsis in a patient, comprising providing the patient with an automatic thermometer that periodically measures the patient's body temperature and transmits a temperature signal that is encoded with the measured temperature value, receiving the temperature signal and automatically comparing the measured temperature value with at least one alarm limit, asserting a warning signal in the event that the measured temperature value bears a predetermined relationship to said alarm limit, determining whether another physiological condition is indicative of onset of sepsis, and, if so, testing the patient for sepsis.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION

Figure 1:
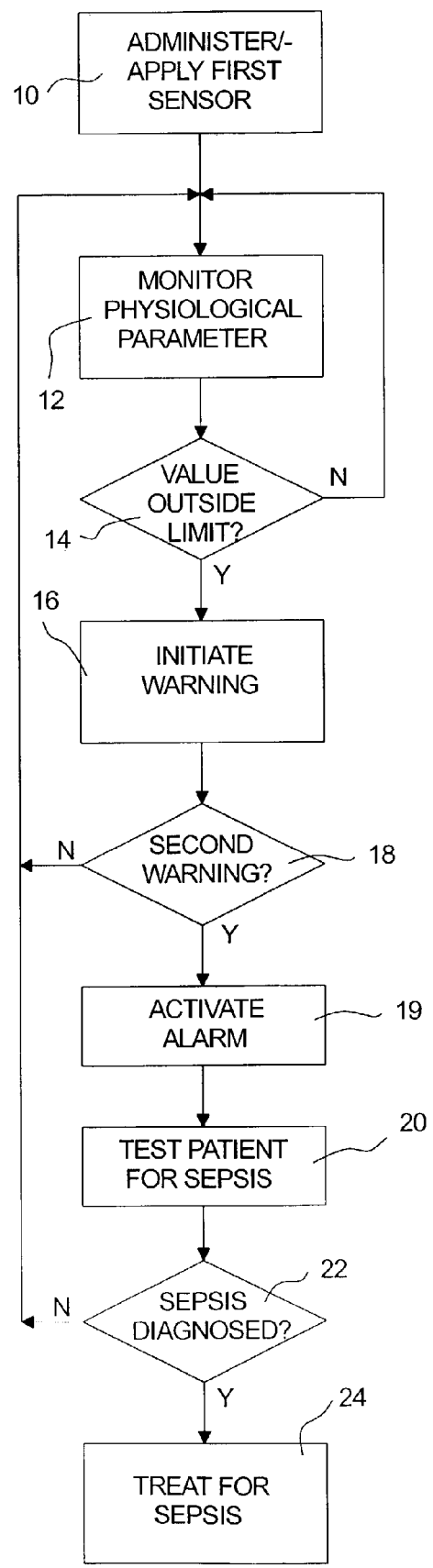
FIG. 1 is a flow chart illustrating the principal steps of a first method embodying the present invention.

In the first method embodying the invention, a patient who is admitted to the hospital is provided with a body temperature sensor, a heart rate sensor and a respiration rate sensor (FIG. 1, step 10).

The body temperature sensor may be the sensor described in U.S. patent application Ser. No. 10/017,098. Preferably the body temperature sensor is implemented in a pill to be ingested by the patient but it may alternatively be implemented in another form, such as a skin patch. In the event that the body temperature sensor is implemented in a pill, the sensor is activated just before it is given to the patient and the patient then swallows the pill. The sensor periodically emits a signal representative of the patient's core temperature.

The heart rate sensor and the respiration rate sensor may be implemented in a skin patch of the general type described in U.S. patent application Ser. No. 10/071,534 but in which the telesensor is configured to acquire an ECG voltage waveform and includes a processor that is programmed to compute a heart rate value and a respiration rate value from the ECG voltage waveform. The telesensor periodically emits a signal that is encoded with the current heart rate and the current respiration rate.

Alternatively, the heart rate sensor may be implemented in a first skin patch including a telesensor that is configured to provide an indication of heart rate and the respiration rate sensor may be implemented in a second skin patch including a telesensor that is configured to provide an indication of respiration rate. The telesensors of the first and second skin patches may each acquire an ECG voltage and calculate the heart rate and respiration rate respectively from the ECG voltage waveform, but alternatively either telesensor may rely on a physiological parameter other than ECG voltage to calculate heart rate or respiration rate, as the case may be.

The patient is also provided with a portable recorder or monitor that accompanies the patient during the patient's hospital stay and includes a receiver unit for receiving the signals emitted by the sensors. A suitable receiver unit for calculating the patient's core temperature from the signal emitted by the ingestible pill is disclosed in U.S. patent application Ser. No. 10/017,098. The recorder monitors the calculated core temperature (step 12) and compares the calculated core temperature with predetermined alarm limits, e.g. a high alarm limit of 38.3° C. (about 101° F.) and a low alarm limit of 35.6° C. (about 96° F.), and asserts a conditional warning signal in the event that the calculated core temperature deviates from the range defined by the alarm limits (steps 14 and 16).

The receiver unit also receives the heart rate signal and the respiration rate signal from the skin patch and compares the heart rate and the respiration rate with predetermined high alarm limits, such as 90 heartbeats per minute and 20 respirations per minute, and asserts a conditional warning signal in the event that either rate exceeds the appropriate high alarm limit (step 18).

The recorder may be provided with an event marker button that may be pressed by a healthcare professional observing the patient in order to record the fact that the patient is exhibiting clinical evidence of infection. When the event marker button is pressed, a circuit in the recorder asserts a conditional warning signal.

If two of the four potential conditional warning signals are asserted concurrently, the recorder emits an alarm signal (step 19), which may be audible and/or visible, in order to alert a responsible healthcare professional of the possible onset of sepsis in the patient. The recorder may also transmit an alarm signal by radio to a nurses' station.

Upon receiving the alarm signal, a nurse or other healthcare professional initiates action, which may be conventional tests, to determine whether there has in fact been an onset of sepsis in the patient (step 20). If sepsis is diagnosed (step 22), treatment is initiated (step 24); otherwise treatment for sepsis is not initiated. In the event that sepsis is not diagnosed, one or more of the alarm limits may be adjusted in order to avoid a further false alarm.

It will be appreciated that although FIG. 1 has been described as if the warning signal asserted in response to the event marker button being pressed were a secondary signal that confirms a conditional warning signal that was previously provided by the temperature sensor, the heart rate sensor or the respiration rate sensor, the warning signal asserted in response to the event marker button being pressed may be the conditional warning signal that is confirmed by a secondary signal provided by one of the electronic sensors.

The splanchnic circulation (blood flow to the small intestine) transfers nutrients from the intestine to the blood and facilitates the transport of the nutrient rich blood to the liver via the hepatic-portal system for the processing of the metabolic nutrients. In addition, the splanchnic circulation provides oxygen and heat to the tissue to facilitate the metabolic process. The splanchnic circulation is about one third of the circulating blood volume of the circulatory system. The splanchnic circulation has a very finely controlled vasoconstriction mechanism that is regulated by the sympathetic nervous system and allows a part of this vast volume of blood to be diverted to other areas of the body during physiological stress.

It is believed that a mechanism by which physiological stress may lead to sepsis is that the vasoconstriction of the splanchnic circulation in response to the stress results in a reduced oxygen delivery to the gut which in turn causes ischemia and death of the cellular membrane of the epithelium, allowing the enteric bacteria to enter the bloodstream.

Based on the foregoing analysis, it appears that a reduction in the splanchnic circulation may be predictive of onset of sepsis. Further, since the delivery of blood to the intestinal tissue regulates intestinal temperature, a change in splanchnic temperature relative to other large tissue masses, primarily muscle, will provide an indirect measure of blood flow to the gut.

In a second method embodying the present invention, a patient entering the hospital is provided with a body core temperature sensor in the form of a pill as described with reference to FIG. 1 (FIG. 2, step 110), a skin temperature patch that is applied to a large tissue mass, such as a large muscle mass or the chest (step 112), and a portable recorder or monitor.

The body core temperature sensor emits a signal that is encoded with the splanchnic temperature and the skin patch emits a signal that is encoded with a temperature that is not directly affected by splanchnic vasoconstriction and vasodilation and serves as a reference temperature for comparison with the splanchnic temperature.

The recorder periodically calculates the difference between the splanchnic temperature and the reference temperature (step 114) and emits an alarm signal in the event that the splanchnic temperature decreases below the reference temperature by an amount that exceeds a predetermined alarm limit (steps 116 and 118). In response to the alarm signal, a healthcare professional initiates action, which may include conventional tests (step 120), to determine whether sepsis has in fact occurred. If sepsis is diagnosed, treatment is initiated (step 122); otherwise treatment for sepsis is not initiated.

Of course, the signal that is initiated in step 118 may be used as a conditional warning, as described with reference to FIG. 1, such that an alarm signal is not issued unless the warning signal is qualified by another warning condition. It will be understood that in this case the physiological parameter that is monitored in step 12, or that gives rise to the second warning (step 18), is the difference between the splanchnic temperature and the reference temperature.

The pacemaker cells in the right atria of the heart determine the intrinsic rate of the heart. However, the heart can be accelerated by the sympathetic nervous system, which releases the neurotransmitter norepinephrine, and the heart can be slowed by the parasympathetic nervous system and its neurotransmitter acetylcholine. Both the sympathetic and parasympathetic nervous system release neurotransmitters on a beat to beat basis to finely regulate heart rate, based on feedback from receptors and from the brain through the central nervous system.

The interbeat interval or IBI (the interval between consecutive beats of the heart) can vary quite widely. An accepted measure of the variability of the IBI is known as the heart rate variability or HRV and is determined by measuring multiple values of the IBI over a test interval and applying a mathematical operation to the IBI values.

In a normal resting individual, the HRV is quite large. As the heart rate increases, for example due to activity of the sympathetic nervous system, the HRV decreases. Since the sympathetic nervous system controls both the heart rate and the vasoconstriction of the splanchnic circulation, it appears likely that a reduction in the HRV may be predictive of a decrease in splanchnic circulation.

Figure 3:
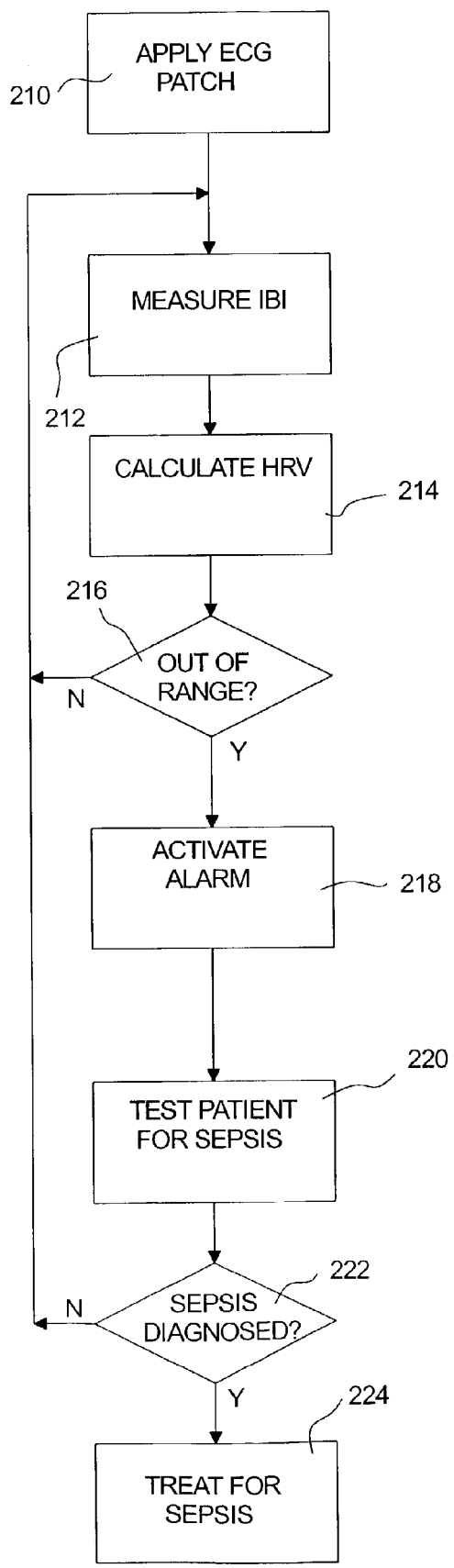
FIG. 3 is a flow chart illustrating the principal steps of a third method embodying the present invention.

In a third method embodying the invention, a patient entering the hospital is provided with a skin patch including a telesensor that is configured to acquire an ECG voltage waveform and includes a processor that is programmed to compute the patient's HRV (FIG. 3, step 210). The telesensor periodically emits a signal that is encoded with the current HRV value.

The patient is also provided with a portable recorder or monitor that accompanies the patient during the patient's hospital stay and includes a receiver unit for receiving the signal emitted by the telesensor. The recorder calculates change in HRV, and may calculate change in HRV relative to other physiological parameters. If the change in HRV exceeds a predetermined alarm limit, the recorder emits an alarm signal and the method proceeds as described with reference to FIG. 2.

Figure 2:
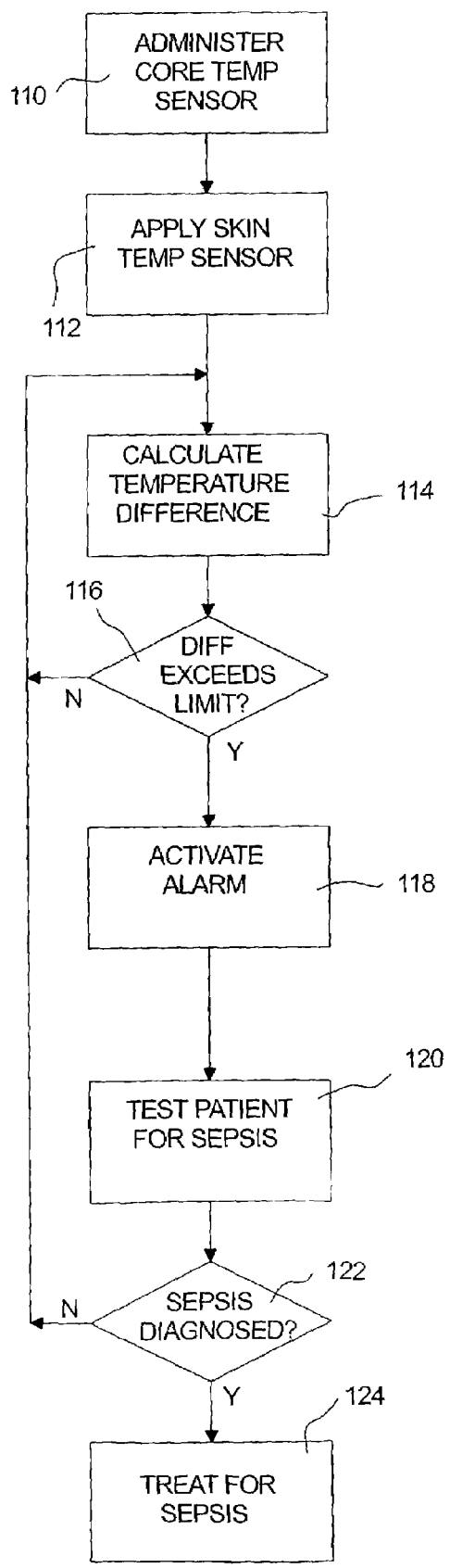
FIG. 2 is a flow chart illustrating the principal steps of a second method embodying the present invention.

Physiological parameters that might be useful input variables for a sepsis alert algorithm that processes the HRV values include core body temperature, heart rate and respiration rate, all of which can be acquired using the skin patch and/or pill referred to in connection with FIGS. 1 and 2.

The alarm signal that is emitted in step 218 may be used as a conditional warning, such that an alarm signal is not issued unless the warning signal is qualified by another warning condition. It will be understood that in this case the physiological parameter that is monitored in step 12 (FIG. 1), or that gives rise to the second warning (step 18), is the change in HRV.

Although the foregoing description of FIG. 2 refers to use of a pill to detect body core temperature and a skin patch to detect a reference temperature that is not directly affected by splanchnic vasoconstriction and vasodilation, it will be understood that the broad idea of using variation in splanchnic temperature as a predictor of potential onset of sepsis is not restricted to the particular mechanisms that are used to detect the body core temperature and the reference temperature. Similarly, although FIG. 3 refers to use of a skin patch including a telesensor that is configured to acquire an ECG voltage waveform, it will be understood that the broad idea of using HRV as a predictor of potential onset of sepsis is not restricted to the particular mechanism that is used to measure IBI.

The methods described above of monitoring vital signs for early warning of the onset of sepsis are ambulatory and would not restrict the patient to any particular healthcare environment (e.g. CCU). The patient would be free to move about the hospital environment or indeed, could be monitored at home, thereby offering a continued protective benefit for the early detection of sepsis, post-hospital environment.

Implementation of this method will have the following benefits:

1. Reduction in mortality rate of sepsis. This condition would be detected earlier, causing healthcare intervention to occur faster, thereby stopping the disease's progression toward possible death of the patient.
2. Early detection of sepsis, along with administration of antibiotics, will greatly enhance the patient's recovery pace at the hospital, speeding his discharge from the hospital, thereby lowering the overall healthcare cost.
3. The methods could be deployed to the patient's home thereby offering a continued protective benefit for the early detection of sepsis, post-hospital environment.
4. Continuous patient vital signs monitoring with alarm signaling will reduce the need for periodic vital signs monitoring conducted manually by a nurse and thereby decrease the nurse to patient contact time. This would represent a productivity improvement for the nurse and hospital.

It will be appreciated that the invention is not restricted to the particular embodiments that have been described, and that variations may be made therein without departing from the scope of the invention as defined in the appended claims and equivalents thereof. Unless the context indicates otherwise, a reference in a claim to the number of instances of an element, be it a reference to one instance or more than one instance, requires at least the stated number of instances of the element but is not intended to exclude from the scope of the claim a structure or method having more instances of that element than stated.

The invention claimed is:

1. A method of screening for possible onset of sepsis in a patient, comprising:
   (a) providing the patient with a first transducer that automatically measures core body temperature and intermittently transmits a first signal that is encoded with the measured value of core body temperature,
   (b) providing the patient with at least one transducer that automatically measures heart rate and respiration rate and intermittently transmits at least one signal that is encoded with the measured values of heart rate and respiration rate,
   (c) receiving the signals transmitted by the transducers and automatically comparing the measured values of core body temperature, heart rate and respiration rate with respective alarm limits, and
   (d) issuing an alarm signal in the event that at least one of the measured values bears a predetermined relationship to its alarm limit and the patient also exhibits at least one of redness around an infection site, swelling and facial pallor.

2. A method according to claim 1, wherein said first transducer is implemented in an ingestible thermometer.

3. A method according to claim 1, wherein step (b) comprises providing the patient with first and second transducers that automatically measure heart rate and respiration rate respectively and intermittently transmit second and third signals that are encoded with the measured values of heart rate and respiration rate.

4. A method according to claim 3, wherein said second and third transducers are implemented in a removable skin patch.

5. A method according to claim 1, wherein step (b) comprises providing the patient with a transducer that acquires an ECG signal, automatically measures heart rate and respiration rate based on characteristics of the ECG signal, and transmits at least one signal that is encoded with the measured values of heart rate and respiration rate.

6. A method according to claim 1, further comprising:
   (a) in the event that the alarm signal is issued, testing the patient for sepsis.

* * * * *